United States Patent [19]

Maldonado et al.

[11] Patent Number: 4,533,634
[45] Date of Patent: Aug. 6, 1985

[54] TISSUE CULTURE MEDIUM

[75] Inventors: Reynaldo L. Maldonado; Kenneth A. Rosanoff, both of Seguin, Tex.

[73] Assignee: AMF Inc., White Plains, N.Y.

[21] Appl. No.: 461,016

[22] Filed: Jan. 26, 1983

[51] Int. Cl.³ .................. C12N 5/00; C12N 5/02; A61K 35/14; A23J 1/06
[52] U.S. Cl. ................... 435/240; 435/241; 424/101; 260/112 B
[58] Field of Search ............... 435/240, 241, 244, 243; 260/112 B; 424/101

[56] References Cited

U.S. PATENT DOCUMENTS

| | | | |
|---|---|---|---|
| 3,122,476 | 2/1964 | Gaeta | 435/240 |
| 3,128,228 | 4/1964 | Michl | 435/240 |
| 3,429,867 | 2/1969 | Bozicevich | 260/112 R |
| 3,686,395 | 8/1972 | Stephan | 424/101 |
| 4,038,139 | 7/1977 | Birch | 435/241 |
| 4,059,512 | 11/1977 | Harris | 424/101 |

FOREIGN PATENT DOCUMENTS

WO82/02900 9/1982 PCT Int'l. Appl. .

OTHER PUBLICATIONS

Fisher et al., *Biochemistry*, vol. 44, pp. 4–10, 1958.
Puck et al., *PNAS*, vol. 59, pp. 192–199, 1968.
Ham et al., in *Methods in Enzymology*, vol. 58, pp. 77–93, 1979.
Temin et al., in *Growth Nutrition and Metabolism of Cells in Culture*, vol. I, Academic Press, NY., pp. 49–81, 1972.
Hayashi, I. et al., *Nature*, vol. 259, No. 5539, pp. 132–134, 1976.
Parker, *Methods in Tissue Culture*, Harper & Row, NY, p. 193, 1961.

*Primary Examiner*—Thomas G. Wiseman
*Assistant Examiner*—Jayme A. Huleatt
*Attorney, Agent, or Firm*—David E. Dougherty; Michael E. Zall

[57] ABSTRACT

A growth factor containing serum is disclosed which is derived from natural bovine serum is disclosed which is by precipitating a first solids fraction from natural bovine serum by adding ammonium sulfate to about 25% saturation to give a first solids fraction and a first supernatant; separating the first solids fraction from the first supernatant; precipitating a second solids fractions from the first supernatant by adding ammonium sulfate to about 40% saturation to give a second solids fraction and a second supernatant; separating the second solids fraction from the second supernatant; combining the first solids fraction and the second supernatant; and desalinating the first solids fraction and the second supernatant, either before or after combination thereof.

9 Claims, 1 Drawing Figure

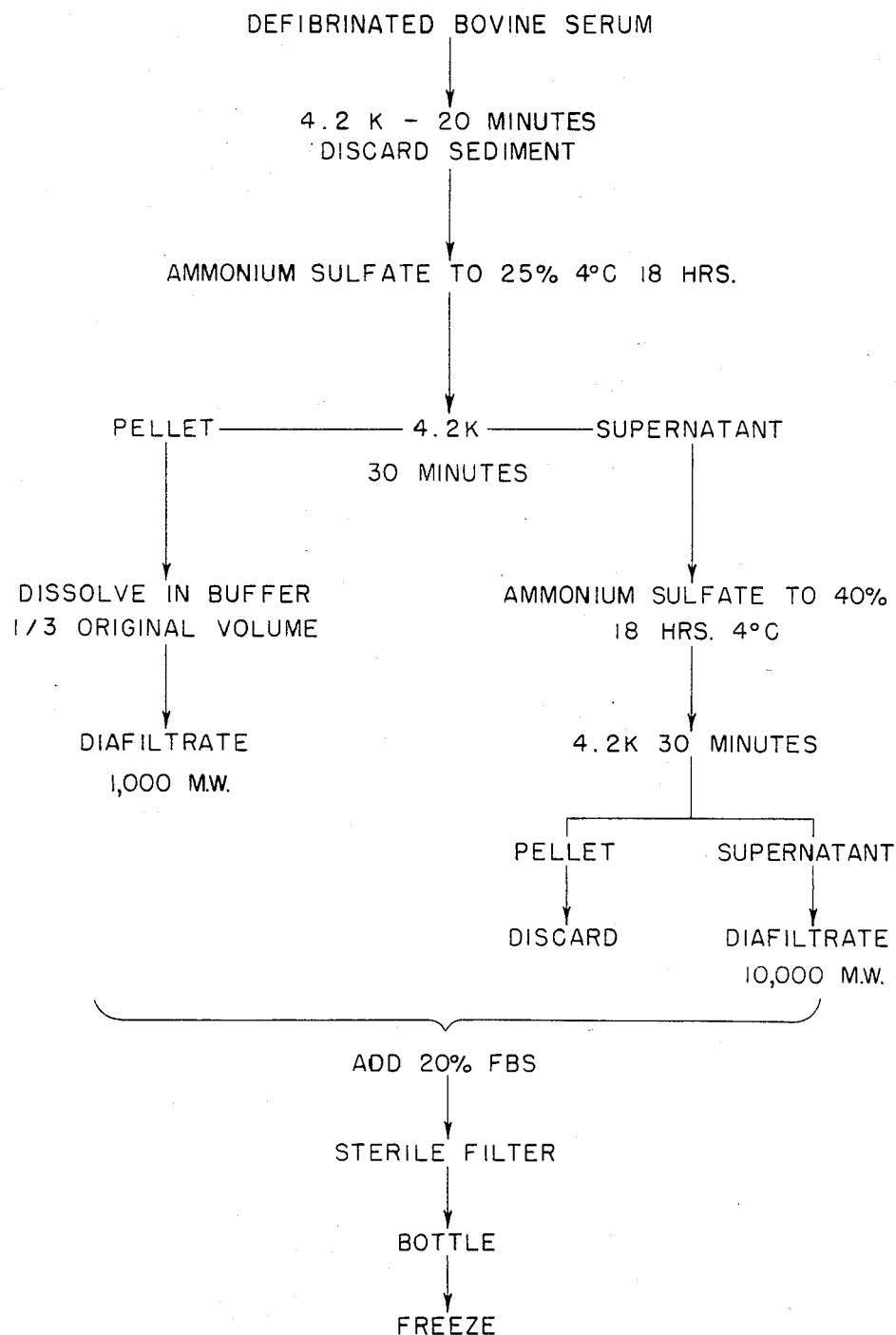

TISSUE CULTURE MEDIUM

BACKGROUND OF THE INVENTION

1. Field of the Invention

The present invention relates to tissue culture media useful for the in vitro growth of cells.

2. Description of the Prior Art

It is well-known that animal and plant cells may be grown in vitro in liquid culture media, i.e., tissue culture; see e.g., Kruse et al, Academic Press, New York, N.Y., 1973, and Ham, R. G. and McKeehan, W. L., Methods in Enzymology, 58; 44–93 (1979). Such media usually contain a wide array of different components, including various nutrients and salts which promote the maximum growth of the cultured cells.

Cells grown in tissue culture are used for many different purposes; for example, for the production of enzymes, cell products, antibodies, or for the general testing of drugs, carcinogenic agents and the like. In vitro growth of animal cell lines has recently acquired new relevance with the development of cell fusion, and the preparation of hybridomas and their associated monoclonal antibodies.

The art has long established that one of the essential components for tissue culture media is bovine serum, most preferably fetal calf or newborn calf serum. These two types of serum lack high concentrations of components which inhibit cell growth, and contain undefined factors which support cell growth in vitro. The use of fetal calf serum, however, is troubled by a lack of sufficient supply, and poor characterization of its ingredients. Furthermore, costs for this type of serum have prevented the economic growth of cells containing such serum.

A number of fetal calf serum substitutes have been proposed. For example, Michl, U.S. Pat. No. 3,128,228, discloses a culture medium for the preparation of tissue cultures on the basis of serum protein fractions, and a nutrient solution containing nutrient salts, protein fission products, and particular amino acids, further sugars and vitamins or coenzymes. The serum substitute is derived from calf blood by coagulation, isolation of the serum, followed by a series of precipitation steps.

Bozicevich, U.S. Pat. No. 3,429,867 describes a so-called "Agamma" calf serum suitable for tissue cultures, prepared from calf serum by precipitation and acidification thereof.

Birch, U.S. Pat. No. 4,038,139 describes a culture medium containing swine serum and about 0.1% of a surfactant which inhibits the precipitation of protein. The swine serum of Birch is stated to support the growth of lymphoid cells giving superior yields to those obtained using fetal calf serum. Swine serum is also considerably less expensive and thus brings about a concomitant reduction in cost.

Gaeta, U.S. Pat. No. 3,122,476, describes a substitute fetal calf serum useful for the growth of normal human cells and other animal cells in vitro, prepared from the blood of immature calves by fractionation, isolation of the serum and separation therefrom of gamma-globulins and other toxic substances by ethyl alcohol precipitation.

The difficulties with one or more of these prior art sera is that extensive and unselective precipitation by salt, acid or organic solvents causes the removal of essential growth factors which render the resulting substitute sera effective for only relative short periods of time; i.e., some of these sera are unable to support cell growth over many generations. Furthermore, it is well-known that calf serum contains a number of toxins not present in fetal calf serum, which toxins tends to inhibit cell growth. An additional disadvantage encountered in some of these sera is the lack of complete standardization of components, which would provide controllable conditions for cell growth in tissue cultures.

A need, therefore, continues to exist for a standardized, well-characterized fetal calf serum-substitute derived from calf serum, which contains active growth ingredients and lacks cell growth inhibiting toxins.

SUMMARY OF THE INVENTION

It is, therefore, an object of the invention to provide a highly efficient tissue culture medium derived from calf serum.

It is another object of the invention to provide a tissue culture medium which is well-characterized and will permit controlled growth of animal and plant cells in vitro.

It is a further object of the invention to provide a tissue culture medium particularly suited for the growth of hybridoma cells.

Yet another object of the invention is to provide a process for the production of a tissue culture medium.

Still another object of the invention is to provide a method for the growth of animal and plant cells in vitro, by utilizing the culture medium of the invention.

These and other objects of the invention as will hereinafter become more readily apparent have been attained by providing a natural bovine serum-derived serum prepared by adding ammonium sulfate to natural bovine serum to about 25% saturation to give a first solids fraction and a first supernatant; separating said first solids fraction from said first supernatant supernatant; adding ammonium sulfate to said first supernatant to about 40% saturation to give a second solids fraction and a second supernatant; separating said second solids fraction from said second supernatant; combining said first solids fraction and said second supernatant; and desalinating said first solids fraction and said second supernatant, either before or after said combining.

These objects have also been attained by providing a method for the growth of animal and plant cells in vitro which comprises culturing said cells in the presence of the aforementioned serum.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawing, wherein:

The FIGURE shows a flow chart which describes production of a serum of the invention from bovine calf serum.

DESCRIPTION OF THE PREFERRED EMBODIMENTS

The present inventors have discovered that if a natural bovine serum is treated with a relatively low concentration (about 25% of the saturation level) of ammonium sulfate, a first solids fraction containing growth factors precipitates from solution. If the ammonium sulfate concentration of the supernatant is increased to about 40% of saturation, a second solids fraction precipitates. This fraction, however, contains factors which inhibit rather than promote growth. Accordingly, the second solids fraction is discarded. The first solids fraction and the second supernatant are desalinated (i.e., the salt, in this case ammonium sulfate, is removed) and combined to give a growth-factor-containing serum of the invention. When the process of the invention is followed to give the desired product sera, it is not necessary to delipidize or otherwise treat the same as has been done in other methods of preparing serum for use in tissue cultures. The sera of the invention are highly useful substitutes for fetal calf sera during the culturing of animal and plant cells in vitro, particularly hybridoma cells. The sera of the invention have low toxicity towards such cells, and allow controlled culture of such cells for extended periods of time.

Probably the single most significant obstacle to researchers engaged in hybridoma research and production of hybridomas is the unavailability of fetal bovine serum of reproducible quality. Presently when a researcher needs serum he requests several samples from several companies. He then subjects the samples to a variety of serum screening processes in hopes of finding at least one specimen of superior quality for hybridoma research. He may be unlucky and find none of acceptable quality. The serum screening process may take several weeks or longer to conclude. When the researcher does find a suitable serum, he then must purchase a larger amount in order to ensure that he does not exhaust it too quickly and have to go through the screening process again. If the researcher is not in a financial position to be able to purchase a large amount of expensive fetal bovine serum, he is doomed to frequent screening. Finding a superior serum from one company does not ensure that the next lot will be of equal quality so that the screening usually must involve samples from several companies.

This dilema makes the serum of the present invention, which is particularly suited for supporting growth of hybridoma cells, of tremendous significance. The inventors have prepared a small scale preparation of quality equal to or better than several samples of fetal bovine serum (FBS). Furthermore, when the procedure was scaled up to produce 20 liters, again a serum equal to or better than FBS in supporting hybridoma growth was obtained. In a third preparation on an even larger scale (90 liters) again a serum of quality better than FBS was obtained. This third preparation was even superior to the first scaled-up preparation. The two large scale preparations are discussed in the Examples as Serum A (20 liter scale) and Serum B (90 liter scale). The superiority of the third preparation is believed to be caused by diafiltration of the 25% addback with 1000 MW pore cartridges rather than the previously used 10,000 MW pore catridges, thus retaining more low molecular weight growth factors. The high quality obtained at any scale indicates that a hybridoma serum of quality superior to most fetal bovine sera can consistently be prepared according to the method of the invention.

The phrase "natural bovine serum" as used in this invention includes serum obtained from cattle by any means which has not previously been treated in any manner intended to purify or separate protein components thereof, except for those steps normally carried out in the preparation of serum from whole blood.

The term "lipids" as used in this invention includes generally the alcohol and ether soluble constituents of serum which are insoluble in water. They comprise the fats, fatty acids, fatty oils, essential oils, waxes, steroids, phospholipids, glycolipids, sulfolipids, aminolipids, and chromolipids (lipochromes). The term also includes lipoproteins, triglycerides, as well as the lipid containing envelopes and membranes of mycoplasma.

The term "endotoxin," also known in the art as "bacterial pyrogen," as used in this invention, refers to the heat stable toxins present in the bacterial cell but not in propagating cultures of intact bacteria, and which are usually released from said bacteria by autolysis upon bacterial cell death. Endotoxins are found primarily in enteric bacilli, but are also found in certain of the gram negative cocci. Endotoxins are pyrogenic, increase capillary permeability, and have profound effects on cell growth, particularly lymphoid cells. The activity is substantially the same regardless of the species of bacteria from which they are derived.

The term "pesticide" includes normally occurring chlorinated pesticides and organophosphate pesticides of various types, such as α and β isomers of 1, 2, 3, 4, 5, 6, hexchlorocyclohexane, aldrin or TDE (tetrachlorodiphenylethane).

Table 1 compares the ranges of biochemical components of the sera of the invention, including preferred sera, (a) with similar components present in natural sera from donor calves less than 1 year old, (b) with natural sera from newborn calves (two sources), and (c) with natural sera from fetal calves. The Table demonstrates that the sera of the present invention is biochemically distinct from the corresponding natural products. In some cases (i.e. enzymes) the normal values reflect parameters that are intentionally left unmodified in the sera of the invention.

TABLE 1

| Profile | Serum of Invention | Donor Calf[1] Serum | Newborn Calf[2] Serum | Fetal Calf Serum |
|---|---|---|---|---|
| Total Lipids mg/dl | 150 | 400[4] | 300 | 300 |
| Total Protein | | | | |
| Content g/dl | 2–4 | 6 | 4–5 | 3.5 |
| Albumin g/dl | 1–3 | 2.5 | 2.2 | 3.5 |
| α-Globulin g/dl | 0.4–2.0 | 1.0 | 1.0 | 1.0 |
| β-Globulin g/dl | 0.4–2.0 | 0.7 | 0.75 | 0.4 |
| γ-Globulin g/dl | 0.1–1.0 | 1.5 | 0.7 | — |
| Cholesterol mg/dl | 50–100 | 80 | 60 | 25 |
| Triglycerides mg/dl | 20 | 35 | 22 | 23 |
| Hemoglobin mg/dl | ND[5] | 25 | 35 | 60 |
| Uric Acid mg/dl | 0–1.0 | 0.2 | 0.8 | 2.5 |
| Cortisol g/dl | ND | 15 | ND | 0.4 |
| Enzymes | | | | |
| Alkaline Phosphatase mu/ml | 100–150 | 100 | 200 | 230 |
| GGT mu/ml | 10–30 | 30 | 260 | 16 |

TABLE 1-continued

| Profile | Serum of Invention | Donor Calf[1] Serum | Newborn Calf[2] Serum | Fetal Calf Serum |
|---|---|---|---|---|
| SGOT mu/ml | 5–20 | 1 | 20 | 50 |

[1]Commercially available from Flow Inc.
[2]Commercially available from Flow Inc.
[3]Commercially available from KC Biol. Inc.
[4]The values given may range to ± 10%
[5]Not determined.

The process for the production of one or more of the sera of the invention comprises precipitating a first solids fraction from natural bovine serum by adding ammonium sulfate to 15–30%, preferably 20–28%, and most preferably 25% saturation to give a first solids fraction and a first supernatant; separating said first solids fraction from said first supernatant; precipitating a second solids fractions from said first supernatant by adding ammonium sulfate to about 30–50%, preferably 38–42%, and most preferably 40% saturation to give a second solids fraction and a second supernatant; separating said second solids fraction from said second supernatant; combining said first solids fraction and said second supernatant; and desalinating said first solids fraction and said second supernatant, either before or after said combining.

The preparation of bovine serum from bovine blood is generally well-known in the art and will not be described in great detail. Any process of preparing serum from calf blood is useful to prepare the sera of the invention.

Calves, preferably feedlot calves of either sex, either grain fed or grass fed, preferably grain fed and preferably being less than 1 year old are bled according to standard practice in the art. Serum from feedlot calves has heretofore been considered unusable for tissue culture media without extensive treatment to remove lipids from the serum. This invention, however, has surprisingly made this serum source more easily usable.

Red blood cells are first separated from the blood, for example, by centrifugation. The supernatant plasma is then clotted, for example, by addition of bovine thrombin and calcium, if necessary. Alternatively, blood can be simply allowed to clot if care is taken to prevent red blood cell lysis. The serum is separated by filtration or centrifugation from the clotted blood, and is ready for further process steps which serve to further refine the product.

Prior to the salt precipitation steps of the invention, it is helpful to centrifuge the defibrinated bovine serum, particularly if it has been stored in frozen form, to remove suspended particles. Adjustment of the protein concentration to 4.2–4.8, preferably 4.4–4.6, and most preferably 4.5 g/100 ml prior to the salt precipitation steps is necessary in order to ensure reproducibility of serum production.

Several essential steps of the present invention involve the precipitation of various protein fractions by controlling the concentration of added salts. Methods of carrying out the individual salt precipitation steps are well-known in the art and are, for example, described in Michl, U.S. Pat. No. 3,128,228 or Birch, U.S. Pat. No. 3,429,867, which are herein incorporated by reference. Any salt capable of precipitating proteins can be used in the invention, such as ammonium sulfate, potassium sulfate, or sodium sulfate, with ammonium sulfate being particularly preferred. The precipitation is carried out at 0° C. to room temperature by slowing adding the salt to a stirred solution of the serum, up to the prescribed levels of salts. For example, in the first precipitation step it is preferred to add ammonium sulfate to about 25% of saturation to serum whose pH has been adjusted (if necessary) to a range of 7–8. Other salts and concentrations which produce the same precipitation reaction are contemplated as equivalents. After the salt is fully dissolved, the solution is gently stirred for from 4 to 24 hours and the precipitated protein and other substances are separated by filtration or centrifugation. Centrifugation at 4,000×g for 30 minutes is preferred. The precipitated protein is retained for later addition back to the last (second) supernatant. The first supernatant is then treated by adding additional ammonium sulfate to a final concentration preferably at about 40% of saturation. This causes undesirable proteins and other substances to precipitate, which can then be discarded. The resulting supernatant, obtained as described above, is eventually combined with the first precipitate to give the serum useful for hybridoma culture media.

After salt additon and protein precipitation, it is necessary to remove salt which remains dissolved in the supernatant or precipitated solids fraction; i.e., to desalinate the solid or supernatant that is being retained. This is normally done by dialysis, diafiltration, gel filtration, or any other such known method, either before or after combination of the fractions being retained. Retention of proteins having a molecular weight of greater than 10,000, preferably greater than 5,000, and most preferably greater than 1000, is preferred during the desalination process. Diafiltration using an appropriate cartridge to effect these molecular weight retentions is the preferred method of desalination.

While additional purification steps are possible, a minimum serum of this invention can be prepared by a process consisting essentially of the above precipitation and desalination steps.

Removal of endotoxin occurs in the salting out steps, endotoxin being removed with the second solids fraction that is precipitated from the first supernatant by increasing the salt concentration to about 40% of saturation. Accordingly, no further treatment to remove endotoxin is required. The levels of endotoxin can readily be followed using commercially available methodology if desired. Most preferred is the Limulus amoebocyte lysate assay.

An additional and optional refining step for the serum is treatment thereof with charcoal in order to remove steroids and other hormones, as well as other toxic products. The term charcoal includes wood-derived or lignite-derived activated carbon. In this step, it is important to work with serum which has normal salt concentration. Thus, if a salt fractionation step preceded charcoal treatment, it is necessary, prior to charcoal treatment, to remove the salt, as by dialysis of diafiltration. Charcoal treatment of the serum can be batchwise or by immobilizing the charcoal on filter mats or pads. When used batchwise, charcoal is added to a well-stirred sample of serum to a range of from 20 to 200 g/l, preferably 50–100 g/l, most preferably at 70 g/l. The charcoal-containing serum can be stirred for a period of from 1 hour to 48 hours from 0° C. to room temperature. The pH should be adjusted to the range of from 5 to 10.5. After settling, the charcoal is separated, e.g., by centrifugation or filtration, making sure that a clear supernatant serum is obtained in the filtrate.

When the charcoal is immobilized in mats or pads, these may be loaded on a cylindric column and the serum simply flowed therethrough at an appropriate rate. This allows a continuous process. Charcoal-containing mats, prepared by physically entrapping powdered charcoal in filter pads can be used. The use of charcoal pads, using about one pad per liter (70–200 g charcoal/pad) with a repeat cycle of the serum therethrough is preferred to the batch method.

An additional optional treatment is heat inactivation at 50°–60° C. for about 20–40 minutes lowers the toxicity of the serum. This occurs because many toxic serum components, such as complement proteins are inactivated at relatively low temperatures.

The most highly refined serum of the invention is that wherein starting serum has been salt fractionated, desalinated, charcoal treated and heat inactivated. The last two steps can be carried out in either order.

As one final measure, the protein content of the sera of the invention can be adjusted by appropriate concentration or dilution so as to adjust the same to the desired controlled range of 2–5 g/dl, preferably about 3 g/dl. At the same time electrolyte levels ($K^+$, $Na^+$, etc.) can be adjusted to any desired level. Preferably, they are set at $[Na^+]=100$–$200$ meq/liter; $[K^+]=1$–$20$ meq/liter; $[Ca^{+2}]=1$–$5$ meq/liter. Most preferably the values at $[Na^+]=150$ meq/liter; $[K^+]=b\ 5$–$6$ meq/liter; $[Ca^{+2}]=3$–$4$ meq/liter. The pH is adjusted to 6–8, preferably about 7.5.

In order to prevent the growth of bacteria or other microorganism, it is necessary to sterilize the sera of the invention, for example, by sterile filtration, prior to storing the final product. Bacterial levels are then undetectable by the assay of *U.S. Pharmacopeia Standards*, Volume 21.

Under these conditions, the sera of the invention are stable indefinitely when frozen at $-20°$ C. or lyophilized. Sera of the invention are particularly easy to lyopholize and reconstitute.

Individual sera prepared at different selected stages of the process are, of course, useful as intermediates in preparing the best, highly refined serum.

The sera of the present invention are useful in all applications wherein fetal bovine serum has been or is used. They can also be used as replacement for other growth media of the art, such as those indicated in Ham, R. G. and McKeeham, W. L., supra, herein incorporated by reference. Normally, the amount of serum in the tissue culture medium is in the range 2–20% by volume, most preferably about 10%. The applications include monolayer cultures, suspended cultures, and clonal cultures. The most important application is that of nutrient source for the tissue culture of animal cells in vitro. Numerous different cell lines may be grown in the present culture media and the method of growing cells is not restricted to any particular cell line. For example, normal cells, transformed cells, and virus-producing cells can be grown with the sera. Particularly, examples of cell lines includes Chinese hamster ovary, mouse, 3T3, chicken embryo fibroblasts, duck embryo fibroblasts, human foreskin, monkey kidney, Syrian hamster kidney, baboon kidney, mouse fibroblasts, BHK, BGM, RD, DET 550, W138, HeLa, mouse lymphocytes, P815 macrocytomas, DS19 erythroleukemia, and the like. The cell lines can be grouped into two broad categories. First are the cell lines which can be grown indefinitely. They usually are transformed or tumor cells. Second are the cells which cannot be grown forever. These cells more closely resemble normal tissue.

The sera of the invention are especially applicable to the growth of hybridomas both from animal and human origin, obtained by the fusion of spleen cells and myelomas and commonly used to prepare monoclonal antibodies. Such fused cell lines are, for example, those described by Kohler et al, Nature 256:495–497 (1975) or in Koprowski et al, U.S. Pat. Nos. 4,172,124 and 4,196,265.

The sera of the invention can be used by themselves ("unspiked" sera) or in combination with natural fetal bovine serum, natural newborn calf serum or any other tissue culture medium or growth factor of the prior art. Particularly preferred are those combinations of the sera of the invention with natural fetal calf serum ("spiked" sera). In such mixtures, the sera of the invention may be present from 1 to 99% and fetal calf serum may be present from 99 to 1% of the mixture volume. Preferred are those mixtures wherein the amount of FCS is such that the functional growth properties of the resulting mixture approximates those of fetal calf serum, depending on the particular cell line system for which it is intended. Most preferred are those mixtures wherein the serum of the invention is present in 50-98%, and FCS is present in 2-50% by volume of the total mixture, particularly those wherein FCS is present at 10–20% by volume. Use of such mixtures is advantageous in that it decreases cost of FCS and extends the range of usefulness of the serum of the invention. The sera of the present invention can also be combined with synthetic media and synthetic growth factors.

In particular, the growth of lymphocytes or leukocyte-type cells in response to mitogen or antigen stimulation is preferably done with unspiked serum, while other cell culture work, such as that used for hydridoma growth or preparation or general cell growth, is preferably done with spiked serum.

When growing cells in vitro, these must be periodically washed free of metabolic waste. If all necessary conditions are met, continuous or transformed cells are capable of living, growing and dividing at a constant rate year after year, and may be alive and fully vigorous many years after the animal or plant from which the tissue cells were taken would have normally died. (See, for example, Giese, "Cell Physiology," 3rd Ed., 1968, 600–601).

Having now generally described this invention, a better understanding can be obtained by reference to certain specific examples which are incorporated herein for purposes of illustration only and are not intended to be limiting of the scope of the invention or the spirit thereof.

EXAMPLE 1

Preparation of a Serum According to the Present Invention

1. Bovine plasma from feedlot calves was clotted by conventional methods, i.e., using calcium and thrombin, and the resulting serum was frozen until needed.

2. The above serum was thawed, centrifuged at 4200 rpm for 20 minutes in a Beckman J6 centrifuge, and the serum was adjusted to a protein concentration of 4.5 g/100 ml.

3. Crystalline ammonium sulfate (A.S.) was added to a concentration of 134.5 g/l (25% of saturation) and mixed overnight.

of the invention to which fetal bovine serum has been added.

The biochemical characterization of the serum from Example 1 is presented in Table 2. This table also incorporates a biochemical analysis of the "Agamma" serum prepared according to Bozicevich, U.S. Pat. No. 3,429,867.

TABLE 2

|  | Units | Serum of Invention | Donor Calf | Newborn[1] Calf | Fetal Calf | Agamma |
|---|---|---|---|---|---|---|
| TEST PROFILE |  |  |  |  |  |  |
| Glucose mg/dl | mg/dl | 0 | 26 | 64 (71) | 140 | 7 |
| Bun mg/dl | mg/dl | 4.0 | 5 | 3 (13) | 14 | 0 |
| Creatomome | mg/dl | 0.9 | 1.0 | 1.1 (1.2) | 3.2 | 0.1 |
| Bun/Creat. Ratio |  | 4.4 | 5 | 3 (11) | 4 | 0 |
| Uric Acid | mg/dl | 1.2 | .2 | .7 (0.9) | 2.4 | 0.0 |
| Sodium | meg/l | 151 | 141 | 139 (140) | 136 | 7 |
| Potassium | meg/l | 6.5 | 5.0 | 7.0 (6.3) | 28 | 0.6 |
| Chloride | meg/l | 112 | 102 | 99 (102) | 99 | 0 |
| Carbon Dioxide | meg/l | 27 | 22 | 31 (21) | 7 | 0 |
| Calcium | mg/dl | 3.2 | 9.5 | 9.7 (7.9) | 13.5 | 4.4 |
| Ion-Ca (Approx) | meg/l | —[2] | 2.1 | 2.5 (1.9) | 4 | 1.3 |
| Phosphorus | mg/dl | 2.5 | 6.4 | 6.7 (5.3) | 10 | 0.1 |
| Cholesterol | mg/dl | 76 | 83 | 54 (65) | 26 | 21 |
| Triglycerides | mg/dl | 20 | 34 | 21 (24) | 23 | 7 |
| Total Protein | gm/dl | 3.7 | 6.9 | 5.3 (6.1) | 3.9 | 3.7 |
| Albumin | gm/dl | 1.9 | 3.0 | 2.8 (2.9) | 2.4 | 2.9 |
| Globulins | gm/dl | 1.6 | 3.9 | 2.5 (3.2) | 1.5 | 0.8 |
| A/G Ratio |  | 1.18 | 0.8 | 1.1 (0.9) | 1.6 | 3.6 |
| Total Bilirubin | mg/dl | 0 | 0.0 | 0.0 (0.4) | 0 | 0.0 |
| Alk Phos | mu/ml | 124 | 97 | 209 (178) | 231 | 1 |
| GGT | mu/ml | — | 30 | 292 (256) | 16 | 5 |
| SGOT | mu/ml | 14 | 1 | 16 (34) | 47 | 19 |
| LDH | mu/ml | 192 | 690 | 153 (890) | 436 | 262 |
| Iron | mcg/dl | — | 169 | 107 (119) | 239 | 62 |
| PROTEIN ELECTROPHORESIS BLOOD |  |  |  |  |  |  |
| Total Protein | g/dl | 3.7 | 6.1 | 4.6 (5.1) | 3.6 | — |
| Albumin | g/dl | 1.9 | 2.52 | 2.24 (2.24) | 2.2 | — |
| Alpha 1 | g/dl | 0.87 | 1.31 | 1.106 (1.09) | 0.9 | — |
| This sample appears to have the Alpha Globulins in a single band. |  |  |  |  |  |  |
| Beta | g/dl | 0.52 | 0.65 | 0.71 (0.83) | 0.04 | — |
| Gamma | g/dl | 0.21 | 1.62 | 0.59 (0.94) | — | — |

[1]The number in parenthesis represent the determination for a New Calf from a different commercial source.
[2]The mark "—" indicates that test results are not available for the indicated test serum.

4. The resulting precipitate was recovered by centrifugation at 4200 rpm for 30 minutes and dissolved in ⅓ volume of buffer. This material was diafiltrated using an Amicon DC 30 fitted with 1000 MW pore cartridges and saved. This fraction is designated the "25% addback" fraction in the following discussion.

5. The supernatant from step 4 was brought to 40% A.S. by addition of 84.5 g/l A.S. and stirred overnight.

6. Precipitated material was removed by centrifugation as before and discarded. The supernatant was diafiltrated as before using 10,000 MW cartridges.

7. The diafiltrated materials from steps 4 and 6 were pooled and the protein concentration adjusted so that addition of fetal bovine serum at 20% resulted in a protein concentration of 3.5 g/100 ml.

8. This final product was sterile filtered, bottled and stored at −20° C.

Steps 3 and 4 resulted in removal of as yet unidentified cell growth factors which were saved. Steps 5 and 6 resulted in removal of unidentified cell growth inhibitors which were discarded. The combination of the 25% addback and supernatant from step 6 resulted in a serum of the invention capable of supporting cellular growth, but supplementation with 20% fetal bovine serum yielded a serum superior to several commercially available fetal bovine sera which were sampled and accordingly, represents a preferred embodiment of the invention. The FIGURE shows a process of preparing the preferred embodiment of the invention, i.e., serum

EXAMPLE 2

Growth factor containing sera of this invention were tested against other sera for ability to sustain growth of various cell lines. Different assay procedures were used to test efficency of the various sera in fusion, hybrid selection, and cloning media normally used in the production of monoclonal antibodies. For example, mouse splenocyctes and mouse myeloma cells (NSI) were fused with polyethylene glycol and plated in a HAT selection medium containing either a serum of the invention or a comparative serum. Fusions comparing various sera were done as identically as possible, and the comparisons shown below were made only to fusions carried out at the same time. Other tests run were comparisons of cloning efficiencies and survival in HAT media of hybrid cells.

Cloning efficiencies were determined for both hybrid and non-hybrid myelomas. Cells were diluted so that a 96-well plate received 32 cells; i.e., 1 cell per 3 wells. This ensured that few if any wells would receive more than one cell. The Poisson distribution was 69 empty wells; 22.7×1-cell wells; 3.8×2-cell wells. Growth media were identical except for the use of the different sera. Dulbecco's Modified Eagle's Medium (DMEM) was used as the base medium throughout unless otherwise stated.

HAT survival was determined in a similar manner except that only hybrid cells were used. The cells were seeded in HAT selection media containing either a serum of the invention or a comparative serum. HAT survival is a more vigorous test of cell survival than cloning since HAT medium is stressful even to surviving cells.

Several comparative tests and their results are shown in the following Tables and related discussions.

TABLE 3

SELECTIVE PRECIPITATE OF GROWTH PROMOTING FACTORS FOR MOUSE 3T3 CELLS

| Serum Component | |
|---|---|
| DLCS #1 + 10% FBS | $5.21 \times 10^6$ Cells/Culture |
| DLCS #1 | 0 Cells/Culture |
| DLCS #1 + 25% Precipitate | $7.86 \times 10^6$ Cells/Culture |
| DLCS #2 | 0 Cells/Culture |
| DLCS #2 + 25% Precipitate | $2.94 \times 10^6$ Cells/Culture |
| Reheis FBS | $8.0 \times 10^6$ Cells/Culture |

Table 3 demonstrates that the addition of 25% addback (25% A.S. precipitate) to sera lacking growth promoting properties renders these sera capable of promoting cellular growth in a manner similar to the addition of FBS. Thus growth enhancing factors from serum are recovered by 25% A.S. precipitation. DLCS is a delipidized calf serum which does not support the growth of mouse 3T3 cells. The base medium used in the first five experiments shown was 90% DMEM and 10% DLCS, with or without various additives. In one experiment, 10% (based on total serum) fetal bovine serum was added (DLCS+10% FBS). In two experiments, the growth factors obtained by a 25% saturation ammonium sulfate (A.S.) precipitation were added. Two batches of DLCS (#1 and #2) were tested. Reheis FBS is a commercially available FBS and was present as 10% of a growth medium based on DMEM (90%). In all cases the beginning cell number was $2.5 \times 10^5$.

TABLE 4

COMPARISON OF AMMONIUM SULFATE PRECIPATES

| SERUM PRESENT IN MEDIUM | 4TH PASSAGE | % OF GREATER | 5TH PASSAGE | % OF GREATER |
|---|---|---|---|---|
| 30/40 + 25% ppt | $7.41 \times 10^6$ | 100% | $3.12 \times 10^7$ | 100% |
| 30/40 + 30% ppt | $5.55 \times 10^6$ | 74.9% | $1.05 \times 10^7$ | 33.6% |

A comparison of growth factors obtained in a 25% of saturation precipitation and a 30% of saturation precipitation was made. Table 4 demonstrates that raising the A.S. concentration used to recover growth factors to 30% results in decreased growth promotion compared to 25% A.S. recovered material. Thus, growth factors present in both 25% and 30% addbacks are inhibited by additional material precipitated by 30% A.S. The cells used were Hela cells, a continuous human carcinoma cell line 30/40+25% ppt is a serum prepared by removing both 30% and 40% solids from a serum and adding back an equivalent amount of 25% precipitate. 30/40+30% ppt is a similar serum except that the precipitate added back was a 30% precipitate. Both sera were present in 10% by volume in 90% DMEM.

TABLE 5

CLONING OF HYBRID IN MEDIA WITH VARIOUS SERA

| SERUM IN MEDIUM | # CLONES | # LARGE CLONES |
|---|---|---|
| 40/25/10% FBS | 94 | 27 |
| 40/25/20% FBS | 127 | 45 |
| SS FBS | 67 | 19 |

TABLE 5-continued

CLONING OF HYBRID IN MEDIA WITH VARIOUS SERA

| SERUM IN MEDIUM | # CLONES | # LARGE CLONES |
|---|---|---|
| M.A. FBS | 99 | 23 |

Table 5 shows a HAT survival assay showing that a small scale preparation of the invention supports the survival of more clones than the compared FBS. The number of large clones was also higher in the serum of the invention. The base medium was 85% DMEM and 15% of the designated serum. 40/25/10% FBS is a serum prepared with the 40% A.S. supernatant to which the 25% A.S. precipitate has been added back which contains an additional 10% (based on total serum) of fetal bovine serum. 40/25/20% FBS is the same initial serum but contains 20% FBS. SS FBS is a commercial fetal bovine serum from Sterile Systems. M.A. FBS is a commercial fetal bovine serum from Microbiological Associates.

TABLE 6

HAT SELECTION OF HYBRIDS IN VARIOUS SERA

| SERUM IN MEDIUM | # CLONES | # LARGE CLONES |
|---|---|---|
| 40/25/10% FBS | 101 | 40 |
| 40/25/20% FBS | 109 | 28 |
| SS FBS | 53 | 19 |
| M.A. FBS | 26 | 9 |

Table 6 shows a HAT selection assay of polyethylene glycol fused hybrids in 85% DMEM medium with the various sera (15%) listed in Table 5. The number of clones surviving HAT selection was higher in the preparation of the invention, and again the number of large clones was higher.

TABLE 7

FUSION AND HAT SELECTION IN VARIOUS SERA

| FUSION AND STABILIZATION IN SS FBS | | |
|---|---|---|
| Selected in: | SS FBS | Serum of Invention |
| # clones | 35 | 84 |
| # large clones | 20 | 55 |
| FUSION AND STABILIZATION IN MA FBS | | |
| Selected in: | MA FBS | Serum of Invention |
| # clones | 20 | 49 |
| # large clones | 8 | 26 |
| FUSION AND STABILIZATION IN SERUM OF THE INVENTION | | |
| Selected in: | SS FBS | MS FBS | Serum of Invention |
| # clones | 66 | 37 | 67 |
| # large clones | 39 | 19 | 50 |

Table 7 shows a comparison of fusion and HAT selection support by the various sera listed in Table 5. "Fusion and Stabilization" indicates that the myeloma cells were cultured before fusion and after fusion in the indicated serum. "Selected in" indicates HAT selection of these fused cells in the indicated sera. When cells were selected in the serum of the invention, the number of clones and size of clones was higher regardless of which serum was used in fusion and stabilization. "Serum of Invention" was the first scaled up pilot of 20 liters (40% supernatant +25% precipitate, spiked with 20% FBS). The base medium was 85% DMEM with 15% serum.

TABLE 8

CLONING EFFICIENCY ASSAY

|  | SERUM OF INVENTION | | M.A. FBS | S FBS |
|---|---|---|---|---|
|  | EXPT. 1 | EXPT. 2 | | |
| POSITIVE WELLS | 18 | 20 | 19 | 17 |
| NO. OF CLONES | 19 | 22 | 21 | 22 |
| NO. OF LARGE CLONES | 15 | 12 | 18 | 21 |

Ave. .33 cells/well
Poisson distribution 69.0 empty wells; 22.7 1-cell wells; 3.8 2-cell wells; .413-cell wells.

Table 8 shows a cloning efficiency assay of NSI mouse myeloma cells in 85% DMEM medium without HAT but with the three sera (15%) discussed in Table 7. This test is commonly used to screen sera but is not very strenuous on the cells. Thus sera which score well in this test might not do as well in the more strenuous HAT survival or fusion and selection tests. Sera of the invention in duplicate tests scored about equal to the FBS samples compared.

TABLE 9

HAT SURVIVAL ASSAY

|  | SERUM OF INVENTION | M.A. FBS | SS FBS |
|---|---|---|---|
| POSITIVE WELLS | 92 | 91 | 94 |
| NO. OF CLONES | 316 | 289 | 317 |
| NO. CF LARGE CLONES | 98 | 93 | 68 |

Ave. 5 cells/well

Table 9 shows a HAT survival assay comparing the three sera discussed in Table 7. An average of 5 cells were seeded per well of a 96 well tray. The serum of the invention was as good as either of the FBS samples compared. The base medium was 85% DMEM with 15% added serum.

TABLE 10

HAT SURVIVAL ASSAY

|  | SERUM OF INVENTION B | SERUM OF INVENTION A | SS. FBS |
|---|---|---|---|
| POSITIVE WELLS | 18 | 14 | 16 |
| NO. OF CLONES | 20 | 16 | 18 |
| NO. OF LARGE CLONES | 17 | 11 | 4 |
| CLONING EFFICIENCY | 74.40 | 59.52 | 66.96 |

Ave. .28 cells/well × 96 well = 26.88 cells
Cloning Efficiency = $\frac{\text{No. of clones}}{26.88}$
Poisson distribution 72.6 = 0 Cells; 20.3 = 1 Cell; 3 = 2 Cells Table 10 shows a HAT survival assay using a lower cell number. The lower cell number puts further stress on the cells as cell to cell cooperation in conditioning the medium is eliminated. An average of 0.28 cells/well was seeded in 96 well plates. In this assay a second scaled up pilot serum of approximately 90 liters (serum B) was also compared. Serum B differs from serum A in that the first solids fraction of serum A was diafiltered using a 10,000 MW cut-off filter and the first solids fraction of serum B was diafiltered using a 1000 MW cut-off filter. Serum A (Table 7) and SS FBS were equal except for more large clones in serum A. Serum B was slightly better than Serum A in clones and number of large clones.

The theoretical number of cells per 96-well tray equals 26.88. Since each clone arises from a single cell the 20 clones in Serum B represents a 74.4% cloning effeciency. The base medium was 85% DMEM.

TABLE 11

FUSION AND SELECTION ASSAY

|  | EXP. 1 | | EXP. 2 | |
|---|---|---|---|---|
|  | SERUM B | SERUM A | SERUM B | SERUM A |
| POSITIVE WELLS | 40.5 | 21.5 | 39.5 | 16 |
| NO. OF CLONES | 126.5 | 47.5 | 135.5 | 39 |
| NO. OF LARGE CLONES | 63 | 20.5 | 65 | 10.5 |

Table 11 shows a fusion and selection assay done in duplicate on separate days comparing the two large scale pilot lots. In both cases pilot lot serum B was better than serum A in number of clones and size of clones. The base medium was 85% DMEM.

TABLE 12

HAT SURVIVAL ASSAY

|  | SERUM B | SERUM A |
|---|---|---|
| POSITIVE WELLS | 93.5 | 94.5 |
| NO. OF CLONES | 345 | 309.5 |
| NO. OF LARGE CLONES | 119.5 | 91.0 |
| CLONING EFFICIENCY | 71.88% | 64.48% |

Average 5 cells/well × 96 = 480

Table 12 shows a HAT survival comparison of the two pilot lots. A total of 480 cells (5 cells/well) were seeded. The number of clones and large clones was higher in Serum B. The base medium was 85% DMEM.

TABLE 13

ANTIBODY PRODUCTION IN TEST SERA

| DILUTION | SERUM B | SS. FBS |
|---|---|---|
| 0 | Too high to Measure | |
| ½ | Too high to Measure | |
| ¼ | Too high to Measure | |
| ⅛ | 1.817 | 1.870 |
| 1/16 | 1.221 | 1.312 |
| 1/32 | .750 | .784 |
| 1/64 | .479 | .507 |
| 1/128 | .292 | .300 |

Table 13 shows an assay to determine antibody production by a hybridoma supported by test sera. The hybridoma HFN-7.1A was obtained from ATCC and was adapted to the test sera. Cell numbers were equal before measurement of antibody. The antibody was measured by EIA. The results are optical density measurements. Antibody production by this hybridoma was equal in Serum B and SS FBS. The base medium was 85% DMEM.

TABLE 14

| | GROWTH SUPPORT | |
| --- | --- | --- |
| | SERUM B | SS. FBS |
| PASSAGE #3 | | |
| NSI Myeloma | $1.0 \times 10^6$ Cells/ml | $4.9 \times 10^5$ Cells/ml |
| Hybridoma HFN 7.1A | $6.0 \times 10^5$ | $7.8 \times 10^5$ |
| PASSAGE #4 | | |
| NSI Myeloma | $2.1 \times 10^5$ | $1.5 \times 10^5$ |
| HFN 7.1A | $2.9 \times 10^5$ | $3.8 \times 10^5$ |

Table 14 shows a comparison of growth of NSI mouse myeloma cells and hybridoma HFN-7.1A obtained from the ATCC in Serum B and SS-FBS. Growth rates were equal for both NSI and the hybridoma cells. The base medium was 85% DMEM.

Having now fully described this invention, it will be apparent to one of ordinary skill in the art that the details of formulation or operation thereof can be subject to changes without departing from the spirit of the invention or any embodiments thereof.

What is claimed as new and intended to be covered by Letters Patent of the United States is:

1. A process for producing a growth factor containing serum having a $\gamma$-globulin content of between about 0.1–1.0 g/dl, and of 50–100 mg/dl of cholesterol comprising the steps of:
   (a) adding ammonium sulfate to natural bovine serum to 15–30% saturation to give a first solids fraction and a first supernatant;
   (b) separating said first solids fraction from said first supernatant;
   (c) adding ammonium sulfate to said first supernatant to 35–45% saturation to give a second solids fraction and a second supernatant;
   (d) separating said second solids fraction from said second supernatant;
   (e) combining said first solids fraction and said second supernatant; and
   (f) desalinating said first solids fraction and said second supernatant, either before or after said combining.

2. The process of claim 1, wherein said first solids fraction is obtained by adding ammonium sulfate to 20–28% saturation.

3. The process of claim 1, wherein said first solids fraction is obtained by adding ammonium sulfate to 25% saturation.

4. The process of claim 1, wherein said second solids fraction is obtained by adding ammonium sulfate to 38–42% saturation.

5. The process Of claim 1, wherein said second solids fraction is obtained by adding ammonium sulfate to 40% saturation.

6. The process of claim 1 which further comprises contacting said serum with charcoal.

7. The process of claim 1 which further comprises sterilizing said serum.

8. The process of claim 1 which further comprises heat inactivating said serum.

9. A method of enhancing the cell growth promoting ability of natural bovine serum which comprises treating said serum by the process of claim 1.

* * * * *